United States Patent
Vandevelde et al.

(10) Patent No.: US 6,271,218 B1
(45) Date of Patent: Aug. 7, 2001

(54) METHOD FOR INHIBITING DEOXYRIBONUCLEOTIDE TRIPHOSPHATE BIOSYNTHESIS

(75) Inventors: Michel Vandevelde, Brussels; Hélène Margery, Bierges, both of (BE)

(73) Assignee: Previsan AG, Zug (CH)

(*) Notice: Subject to any disclaimer, the term of this patent is extended or adjusted under 35 U.S.C. 154(b) by 0 days.

(21) Appl. No.: 09/254,652
(22) PCT Filed: Sep. 12, 1997
(86) PCT No.: PCT/BE97/00104
 § 371 Date: Mar. 30, 1999
 § 102(e) Date: Mar. 30, 1999
(87) PCT Pub. No.: WO98/10772
 PCT Pub. Date: Mar. 19, 1998

(30) Foreign Application Priority Data

Sep. 13, 1996 (BE) .................................. 9600772

(51) Int. Cl.[7] .................................. A61K 31/655
(52) U.S. Cl. .................................. 514/150
(58) Field of Search ............................... 514/150

(56) References Cited

U.S. PATENT DOCUMENTS

| | | | |
|---|---|---|---|
| 5,399,555 | 3/1995 | Vandevelde et al. | 514/150 |
| 5,585,367 | 12/1996 | Vandevelde et al. | 514/150 |

FOREIGN PATENT DOCUMENTS 9107876   6/1991  (WO) .
9116054   10/1991 (WO) .

OTHER PUBLICATIONS

R. E. Meyn et al., "Post–Irradiation Treatment of CHO Cells with Diamide Inhibits DNA Strand Break Rejoining," in *Radiation Research*, vol. 94, No. 3 (Jun. 1983), p. 614.

J. F. Ward et al., "Effects of Inhibitors of DNA Strand Break Repair on HeLa Cell Radiosensitivity," in *Cancer Research*, vol. 44, No. 1 (Jan. 1984), pp. 59–63.

*Primary Examiner*—Dwayne C. Jones
(74) *Attorney, Agent, or Firm*—Dykema Gossett PLLC

(57) ABSTRACT

Process for inhibiting deoxyribonucleotide triphosphate biosynthesis by cells, comprising application onto these cells of at least one of the azo derivatives of the formula (I), in which $R^1$, $R^2$, $R^3$ and $R^4$=H, Hal, aliphatic or aromatic hydrocarbon or a nitro group, $R^1$ and $R^2$ as well as $R^3$ and $R^4$ being capable of forming a heterocyclic ring with the N adjacent thereto, $X^1$ and $X^2$=O or $NR^5$, where $R^5$=H, Hal, aliphatic or aromatic hydrocarbon, or a nitro group, and the use of these derivatives for the production of medicines to be administered in conditions which require abnormal production of DNA from the cells

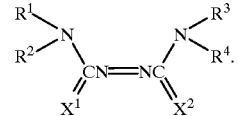

(I)

19 Claims, No Drawings

METHOD FOR INHIBITING DEOXYRIBONUCLEOTIDE TRIPHOSPHATE BIOSYNTHESIS

This application is a U.S. national phase of PCT/BE97/00104, filed Sep. 12, 1997.

BACKGROUND OF THE INVENTION

1. Field of the Invention

The present invention relates to a process for inhibiting deoxyribonucleotide triphosphate biosynthesis by cells, in particular animal, human or plant cells.

2. The Prior Art

It is known that genetic information is carried by the deoxyribonucleic acid (DNA) present in the cell nucleus. DNA comprises a double helix composed of nucleotides, which is fundamental to living organisms, whether animals or plants.

As is known, nucleotides are formed from a sugar, a heterocyclic nitrogenous base and at least one phosphate group. Four phosphates are present in the nucleotides which constitute DNA: deoxyguanidine triphosphate (dGTP), deoxythymidine trisphosphate (dTTP), deoxyadenosine triphosphate (DATP) and deoxycytidine triphosphate (dCTP).

It was noted some years ago that cancerous cells, because they are dividing rapidly, consume a large quantity of nucleotide triphosphates. Research has consequently focused on medicines capable of inhibiting the formation of the deoxyribonucleotides, such as for example 5-fluorouracil, aminopterin and amethopterin (c.f. J. David Rawn, *Biochemistry*, page 648). Hydroxyurea may also be mentioned, which non-selectively inhibits ribonucleotide reductase, and consequently all the nucleotides involved in DNA synthesis (c.f. "DRUG, Facts and comparisons", J.B. Lippincott Company, 1990, pages 2258 and 2259; P. Reichard, "From RNA to DNA, why so many ribonucleotide reductases?", *Science*, volume 260, 1993, pages 1773–1776).

The disadvantage of these products is that, given their lack of selectivity, they inhibit mechanisms which are indispensable to healthy, non-cancerous cells and relate to deoxynucleotides, such as for example intracellular energy transport and the enzymatic reactions catalyzed thereby. Treatment with these products consequently entails considerable toxicity for all cells.

The effect of an analogue of dCTP, cytosine arabinoside or cytarabine, which acts by taking the place of the natural molecule in cellular DNA by means of a competitive phenomenon has already been investigated (c.f. "DRUG" op. cit., pages 2192–2196). This product is not active when taken orally and must be administered with great caution.

Fundamental studies have moreover been undertaken to attempt to combine hydroxyurea with cytarabine. The expected effect was to replace with cytarabine the quantity of dCTP reduced by the action of hydroxyurea (c.f. abstract supplied by the database Medline Express of Schilsky, R. L. et al. "Laboratory and clinical studies of biochemical modulation by hydroxyurea", *Semin. Onc.* Jun. 19, 1992 (3, suppl. 9), 84–89).

Cell lines other than those which are cancerous may have a greatly elevated proliferation rate. Such is the case for lymphocyte cells and the smooth muscle cells of blood vessels during organ transplants (allografts).

Attempts have already been made to control these cells by restricting their level of deoxynucleotides. Mycophenolic acid (MPA) or one of the derivatives thereof which blocks inosine monophosphate dehydrogenase, so bringing about a reduction in intracellular dGTP and consequently blocking DNA synthesis by these cells may be mentioned by way of example (c.f. Pichimayr, R., "Placebo-controlled study of mycophenolate mofetil combined with cyclosporin and corticosteroids for prevention of acute rejection", *The Lancet*, volume 345, May 27, 1995, pages 1321–1325; Sollinger, H. W., "Mycophenolate mofetil for the prevention of acute rejection in primary cadaveric renal allograft recipients", *Transplantation*, volume 60, 225–232, number 3, 1995; Gregory, C. R., "Treatment with rapamycin and mycophenolic acid reduces arterial intimal thickening produced by mechanical injury and allows endothelial replacement", *Transplantation*, volume 59, 655–661, number 5, 1995).

Finally, it is known that viral diseases, in particular AIDS, make significant use of the infected cell's genetic material to replicate the virus. It has recently been discovered that the above-mentioned mycophenolic acid had the ability, given its inhibitory action on the formation of dGTP in cells, to block the activity of reverse transcriptase in vitro and thus to have an anti-HIV effect (V. Hiroshi Ichimura and J. A. Levy, "Polymerase substrate depletion: A novel strategy for inhibiting the replication of the human immunodeficiency virus", *Virology* 211, 554–560, 1995).

The object of the present invention is to provide a process for inhibiting deoxyribonucleotide triphosphate biosynthesis by animal, human or plant cells which does not exhibit the above-stated disadvantages, in particular unacceptable toxicity for healthy cells, and which thus prevents the large-scale and abnormal cellular production of deoxyribonucleic acid, which may result, for example, in cancerous cell proliferation.

SUMMARY OF THE INVENTION

This object is achieved by a process as described above, comprising application onto said cells of at least one of the azo derivatives of the formula

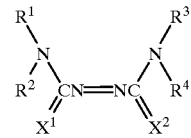

in which $R^1$, $R^2$, $R^3$ and $R^4$ are identical or different and each represent a hydrogen or halogen atom or an optionally substituted aliphatic or aromatic hydrocarbon residue, $R^1$ and $R^2$ possibly being connected together to form a heterocyclic nucleus with the nitrogen atom adjacent thereto, and $R^3$ and $R^4$ possibly being connected together to form a heterocyclic nucleus with the nitrogen atom adjacent thereto, $X^1$ and $X^2$ are identical or different and each represent an oxygen atom or a group $NR^5$, in which $R^5$ is a hydrogen or halogen atom, an optionally substituted aliphatic or aromatic hydrocarbon residue, or a nitro group, and in which, when two groups $NR^5$ are simultaneously present, each $R^5$ may be identical to or different from the other, as well as the isomers thereof.

Various of these azo derivatives are known compounds, in particular for their antiviral activity, in particular against viruses of the retrovirus group, in particular the AIDS virus (c.f. EP-A-0504184 and EP-A-0524961).

1,1-Azobisformamidine and 1,1'-azobisformamide were prepared as long ago as the end of the last century by J. Thiele (c.f. The Merck Index, 10$^{th}$ edition, 919, Rahway, 1983; F. C. Schmelkes et al., "N,N'-dichloroazocarbonamidine (azochloramide), a N-chloro derivative of the oxidant in an oxidation-reduction system", *Journal of American Chemical Society*, 56, 1610, 1934; FR-B-2056874; U.S. Pat. No. 3,225,026; U.S. Pat. No. 3,684,713). 1,1'-Azobisformamide is known as an additive in flour for food use (U.S. Pat. No. 2,903,361). 1,1'-Azobisdimethylformamide has also long been known for its intracellular oxidising action on the glutathione in human blood cells (N. S. Kosower et al., "Diamide, a new reagent for the intracellular oxidation of glutathione to the disulfide", *Biochemical & Biophysical Research Communications*, volume 37, number 4, 1969) and for its initiation of an additional $Ca^{2+}$ efflux from the liver of perfused rats (H. Sies et al., "Hepatic calcium efflux during cytochrome P-450-dependent drug oxidations at the endoplasmic reticulum in intact liver", *Proc. Natl. Acad. Sci. USA*, volume 78, number 6, pages 3358–3362). This substance has also been studied for its inhibition of the repair of small breaks in DNA strands caused by cell irradiation in a hypoxic environment by means of ionizing radiation (R. E. Meyn et al., "Post-radiation treatment of CHO cells . . . ", *Radiation Research*, volume 94, number 3, 1983, page 614; J. F. Ward et al., "Effects of inhibitors of DNA strand break repair . . . ", *Cancer Research*, 44, 1984, pages 59–63). 1,1'-Azobisnitroformamidine has also long been known (W. D. Kumler, "The dipole moments, ultraviolet spectra and structure of azo-bis-(chloroformamidine) and azo-bis-(nitroformamidine)", *Journal of American Chemical Society*, 75, 3092, 1953). Chloroazodin, which is used according to the invention, has also long been known as a disinfectant (c.f. U.S. Pat. No. 2,073,256 and GB-A-421006).

Observing the effects of these substances on cells in vitro and then in clinical trials did not clarify their mode of action on the HIV viruses. Various investigations have been performed to this end. They led to the conclusion that 1,1'-azobisformamide (ADA) does not inhibit reverse transcriptase in a test system containing no cells at concentrations of $CI_{90}$. Simultaneous treatment of $MT_4$ cells with this substance and HIV-1 does not interfere with the integration of proviral DNA. Moreover, ADA did not seem to inhibit Tat transactivation of gene expression induced by LTR of HIV-1 (M. Vandevelde et al., "ADA, a potential anti-HIV drug", *AIDS research & human retroviruses*, volume 12, number 7, 1996, pages 567–568).

This testing has revealed that ADA does not act in the same manner as the known reverse transcriptase inhibitors conventionally used in AIDS treatment, such as AZT, ddI, ddC and others. It acts at an unidentified post-transcriptional stage. It also does not act in the same manner as the 7-chloro-5-(2-pyrryl)-3H-1,4-benzodiazepine-2(H)-one recently developed by the company Roche.

Finally, still more recent trials of ADA have demonstrated that ADA had no protease inhibiting effect at the post-transcriptional stage and thus did not act in the same manner as the protease inhibitors recently used in treating AIDS.

Despite these successive failures to understand the mode of action of ADA on the HIV viruses, a new trial has been set under way to determine whether this substance does not act on the treated cells in the same manner as hydroxyurea. This latter substance is formed from a molecule distantly related to ADA, although it is not an azo derivative.

This comparative trial is described in greater detail in the Examples below.

It would appear from this trial that, on the one hand, ADA does indeed act on the biosynthesis of cellular deoxyribonucleotide triphosphates, which explains its posttranscriptional mode of action on the HIV viruses, but that, on the other, its action differs entirely from that of hydroxyurea. ADA is in fact not a non-selective ribonucleotide reductase inhibitor, but is on the contrary a derivative which acts primordially to inhibit the formation of dCTP present in cells. It should be noted that deoxycytidine triphosphates comprise the group of deoxynucleotide phosphates having the lowest concentration in the cells. A reduction in the content in or selective disappearance of these deoxycytidine triphosphates from the cell thus prevents the cell from biosynthesizing DNA, while requiring for this purpose a substantially lower active substance concentration than that required by hydroxyurea to inhibit all the deoxynucleotides.

Biosynthesis inhibition, which in the case of ADA results in preferential inhibition of the formation of deoxycytidine triphosphates, could proceed as a consequence of ADA acting on different cellular enzymatic targets. It could be predicted that ADA would have an inhibitory action on UMP/CMP kinase (uracil monophosphate/cytidine monophosphate kinase), which would block the formation of deoxycytidine diphosphate (dCDP) from deoxycytidine monophosphate (dCMP), as well as the formation of cytidine diphosphate (CDP) from cytidine monophosphate (CMP). ADA could thus be viewed as having an effect on cytidine triphosphate (CTP) synthetase, which would block the formation of this substance from uracil triphosphate (UTP). Other targets could also be considered, such as for example inter alia NDP kinase, although these are less probable in the specific case of ADA.

Moreover, it should be noted that ADA has long been known to be non-toxic to human beings (c.f. B. L. Oser et al., "Studies of the safety of azodicarbonamide as a flour-maturing agent", *Toxicology & Applied Pharmacology*, 7, 445–472, 1965).

Furthermore, a trial has already been conducted on healthy volunteers who were treated for 30 days with 1500 mg per day of ADA, in three 500 mg of doses, without any side-effects (c.f. EP-0524961, Example 12). Clinical trials were then undertaken. Ten volunteers took ADA for 3 months at dosages of 1 g three times daily for the first month, 2 g three times daily for the second month and 3 g three times daily for the third month. No serious side-effects were observed, apart from one episode of nephritic lithiasis at the 9 g/d dose in one of the patients as a result of a build-up of the catabolite of the product (biurea) in the kidneys.

It is also known that when 1,1'-azobisdimethylformamide is used in the treatment of healthy cells, it has no toxic effect on the cells even at relatively high concentrations (c.f. EP-A-0524961, Examples 9a) and 10a)). This same effect has been observed for 1,1'-azobisdimethylformamide (c.f. EP-A-0524961, Example 8a)) and for 1,1'-azobisformamide (c.f. EP-A-0524961, Example 11a)).

Finally, it is also known that, at concentrations of 660 µg/ml, chloroazodin does not reduce the viability of healthy cells and does not reach the environmental toxicity threshold as determined by acute fish toxicity (c.f. EP-A-0504184, Examples 6 and 12).

It may thus be concluded that the derivatives to be used according to the invention not only allow an action to be exerted upon deoxyribonucleotide triphosphate biosynthesis in the treated cells at relatively low doses, but moreover have very low intrinsic toxicity towards the human body or the healthy cells which are treated.

According to one embodiment of the invention, at least one of the stated azo derivatives is applied onto cells isolated from macroorganisms or onto cells of microorganisms, for example originating from cell cultures. According to the invention, it is also possible to envisage such application onto the cells of an organism or multicellular tissue extracted from a human or animal body, for example onto blood vessel cells or cells from a sample of blood or lymph, as well as onto the cells of a graft which is to be introduced after said application into the body of a human or animal, for example a heart or kidney. A graft may be taken to mean an allograft to be introduced into the body of another human or animal and the extraction of the organism or multicellular tissue may be taken to be definitive. Phytosanitary treatment of plants, for example of seeds or developed plants, may also be considered for treatment with these azo derivatives.

The invention also relates to the use of at least one azo derivative as stated above for the production of medicines for use in the treatment or prevention of human or animal conditions which give rise to large-scale and abnormal cellular production of deoxyribonucleic acid, with the exception of viral diseases, in particular infections by viruses of the retrovirus group. Antineoplastic medicines may in particular be provided, such as medicines to combat liquid and solid tumors, such as antileukemic and antitumor medicines.

The invention also provides a method for therapeutic or preventive treatment of a human or animal body possibly exhibiting large-scale or abnormal cellular production of deoxyribonucleic acid, with the exception of those affected by a viral disease, in particular by an infection with a virus of the retrovirus group, wherein this method comprises the administration to said human or animal body of a therapeutically effective quantity of an active substance selected from among one or more of the azo derivatives of the above-stated formula.

The invention will now be described in greater detail by means of the following, non-limiting Examples.

EXAMPLE 1

Comparative Trial Between ADA and Hydroxyurea

This trial was conducted by the Antiviral Research Laboratory of the Center for Drug Evaluation & Research of the Food & Drug Administration of the United States of America.

Method:

Cells.

Human A3.01 cells were incubated with 0, 10, 100, 200 micromolar concentrations of ADA and with a 100 micromolar concentration of hydroxyurea in RPMI 1640 with the addition of 10% of fetal calf serum, 4 mM of L-glutamine, in a humidified atmosphere of 95% air and 5% $CO_2$.

Cells undergoing logarithmic growth were used for the determinations of deoxynucleotide triphosphates (DNTP) and ribonucleotide triphosphates (rNTP).

Preparation of Cell Extracts for HPLC

After incubation, 60% methanolic extracts were prepared from heat-inactivated A3.01 cells and analyzed as described in Ford, H. Jr. et al., *Cancer Research*, 51, 3733–3740, 1991.

Determination of intracellular rNTP and dNTP pools by HPLC ion exchange gradient.

The cellular ribonucleotides were measured by ion exchange HPLC on Partisil 10 Sax columns as described in Ford et al., op. cit.

The deoxyribonucleotides were determined using sodium periodate in order to eliminate the ribonucleotides; the deoxyribonucleotides were then determined by ion exchange HPLC as described in Hao, Z. et al., *Mol. Pharmacol.*, 34, 431–435, 1988.

Results

Effect of ADA on rNTP pools in A3.01 cells

| Effect of ADA on rNTP pools in A3.01 cells | | | | |
|---|---|---|---|---|
| | UTP* (nmole/$10^{4\ cells}$) | CTP* | ATP* | GTP* |
| ADA ($10^{-6}$ M) | | | | |
| 0 | 0.71 | 0.24 | 2.51 | 0.38 |
| 10 | 0.87 | 0.28 | 2.85 | 0.45 |
| 100 | 1.10 | 0.31 | 2.64 | 0.47 |
| 200 | 0.49 | 0.09 | 1.31 | 0.22 |
| Hydroxyurea ($10^{-6}$ M) | | | | |
| 100 | 1.01 | 0.34 | 3.69 | 0.93 |
| Effect of ADA on dNTP pools in A3.01 cells | | | | |
| (pmole/$10^6$ cells) | dTTP dCTP | dATP | dGTP | |
| ADA ($10^{-6}$ M) | | | | |
| 0 | 39.7 | 12.7 | 50.3 | 17.2 |
| 10 | 39.2 | 6.5 | 53.6 | 19.4 |
| 100 | 40.3 | 6.2 | 52.1 | 17.1 |
| 200 | 19.1 | 2.9 | 22.8 | 15.1 |
| Hydroxyurea ($10^{-6}$ M) | | | | |
| 100 | 21.6 | 3.6 | 9.0 | 19.3 |

*UTP = uracil triphosphate; CTP = cytosine triphosphate; ATP = adenosine triphosphate; GTP = guanosine triphosphate.

The azodicarbonamide compound thus exhibits a preferential inhibitory effect on the dCTP pool (50% inhibition at concentrations of 10 μM and 100 μM).

A higher concentrations, ADA exhibits a more cytotoxic effect, which is evident from the reduction in the rNTP pools and dNTP pools.

Hydroxyurea, a known ribonucleotide reductase inhibitor, is very different from ADA. It reduces the pools of DATP, dCTP and dTTP, while increasing rNTP pools at a concentration of 100 microM. The rNTP/dNTP ratio in cells treated with hydroxyurea (68.2) (reduction in dNTP pools and increase in rNTP pools) in comparison with that observed in untreated cells (24.33), indicates that hydroxyurea is a specific ribonucleotide reductase inhibitor, while the effect of ADA is preferentially specific to the CTP/dCTP ratio.

EXAMPLE 2

The preferential effect of ADA on the intracellular dCTP pools observed in Example 1 has been confirmed by further investigations conducted by the Antiviral Research Laboratory of the Center for Drug Evaluation & Research of the Food & Drug Administration of the United States of America.

Method:

Peripheral human blood cells from healthy donors (peripheral blood monocytic cells=PBMC) are stimulated by phytohemagglutinin (PHA) and are then incubated with concentrations of 0, 50, 100, 200 μmoles of ADA in an appropriate culture medium. The cell extracts were investigated using three different methods.

1) High performance liquid phase chromatography (HPLC) of the complete extract.

2) HPLC analysis of the extracts after destruction of the precursors (uridine triphosphate, cytidine triphosphate, adenosine triphosphate) with periodate.
3) Analysis by a method after F. Poder comprising a determination by detection using specific DNA probes and amplification.

The results are shown in Table 1 below.

TABLE 1

Preferential effect of ADA on dCTP pools in PHA-stimulated PBMC

| Method | HPLC dCTP | Peridate dCTP | F. Poder dCTP | Mean dCTP | Percentage inhibition |
|---|---|---|---|---|---|
| Quantities of ADA ($\mu$M) | | | | | |
| 0 | 3.01 | 1.42 | 1.76 | 2.06 | 0 |
| 50 | 0.09 | 1.16 | 0.88 | 0.71 | 66 |
| 100 | 0.07 | 0.76 | 0.61 | 0.48 | 77 |
| 200 | 0.05 | 0.6 | 0.46 | 0.37 | 82 |

EXAMPLE 3

Investigation of SUP-T1 cells (continuous line of human lymphoblastic cells) which were stimulated by PHA and then treated by doses of 10 $\mu$g and 20 $\mu$g of ADA/ml of culture medium.

The number of cells was standardized to $5 \cdot 10^4$ cells per ml at day 0. Inhibition of proliferation is expressed as the percentage of the proliferation of the control.

Three evaluation methods were used at the Biochemistry & Nutrition Laboratory of the Université Libre de Bruxelles and at this university's Immunology Laboratory.

Incorporation of tritiated thymidine into the cells as a radiographic marker (experiments repeated 8 times).
Colorimetric marking of cell death by MTT (experiments repeated 12 times).
Trypan blue exclusion method, which is an indicator of cell membrane integrity (experiments repeated 8 times).

The results are shown in Table 2 below. There is a distinct effect on the proliferation of a continuous human cell line.

TABLE 2

Inhibition of proliferation of SUP-T1 cells (examination after 48 hours)

| Method | ADA 20 $\mu$g/ml | ADA 10 $\mu$g/ml |
|---|---|---|
| 3H=thymidine 18 h | 39% ± 18 | 15% ± 6 |
| MTT | 43% ± 8 | 19% ± 10 |
| Trypan blue | 37% ± 17 | 24% ± 10 |

EXAMPLE 4

Capsules for Oral Administration
Composition of One Capsule:
500 mg of ADA
10 mg of glycerine monostearate
10 mg of precipitated silicon dioxide
5 mg of magnesium stearate.

This composition is packaged in gelatine capsules in a conventional manner. It is, for example, possible to administer two capsules three times daily to patients exhibiting symptoms of pathological cell proliferation. The capsules may be administered alone or in combination with any other appropriate antiproliferative treatment.

EXAMPLE 5

Coated Tablets

Tablets containing 250 mg of azobisformamidine were produced in a conventional manner using the following excipients: hydroxypropylmethyl cellulose, hydroxypropyl cellulose, titanium dioxide, polyethylene glycol 400, black iron oxide.

These tablets may be administered to bring about an adequate reduction in intralymphocytic deoxycytidine triphosphates (determination by HPC after isolation of lymphocytes).

This treatment will be instituted to induce and maintain remission in acute lymphatic leukemia (lymphoblastic or lymphocytic leukemia) or in myeloblastic leukemia. The active substance is administered alone or preferably in combination with mercaptopurine or azathioprine or any other appropriate drug.

EXAMPLE 6

Injectable Form

An injectable form is prepared from 1 g of dimethylazobisformamide and apyrogenic distilled water with added NaCl.

These forms should be administered, for example, in cases of adenosarcoma, especially generalized adenosarcoma.

This treatment may be combined with azathioprine, 5-fluorouracil or other conventional treatments.

EXAMPLE 7

Cream or Ointment

A cream or ointment is prepared from azobis [chloroformamidine] (chloroazodin) and, as excipient, in particular glycerine, paraffin oil, petrolatum.

This cream may be applied topically as a supportive treatment for skin cancers, for example epidermoid epithelioma.

EXAMPLE 8

Transdermal administration systems for dimethylazobisformamide may also be provided.

These systems may be administered in order to achieve a sustained reduction in intracellular dCTP in patients suffering from Hodgkin's or non-Hodgkin's lymphoma.

This treatment may be combined with injected cytarabine.

It must be understood that the present invention is not in any way limited to the methods and embodiments stated above and that considerable modifications may be made without extending beyond the scope of the attached claims.

What is claimed is:
1. Process for inhibiting deoxyribonucleotide triphosphate biosynthesis by cells, comprising application onto said cells of at least one of the azo derivatives of the formula

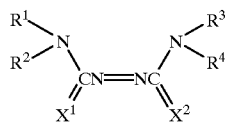

in which $R^1$, $R^2$, $R^3$ and $R^4$ are identical or different and each represent a hydrogen or halogen atom or an optionally substituted aliphatic or aromatic hydrocarbon residue, $R^1$ and $R^2$ possibly being connected together to form a heterocyclic nucleus with the nitrogen atom adjacent thereto, and $R^3$ and $R^4$ possibly being connected together to form a heterocyclic nucleus with the nitrogen atom adjacent thereto, $X^1$ and $X^2$ are identical or different and each represent an oxygen atom or a group $NR^5$, in which $R^5$ is a hydrogen or halogen atom, an optionally substituted aliphatic or aromatic hydrocarbon residue, or a nitro group, and in which, when two groups $NR^5$ are simultaneously present, each $R^5$ may be identical to or different from the other, as well as the isomers thereof.

2. Process according to claim 1, comprising inhibition of the formation of at least one deoxyribonucleotide triphosphate.

3. Process according to claim 2, comprising inhibition of the formation of deoxycytidine triphosphate during said biosynthesis.

4. Process according to claim 1, wherein $R^1$ to $R^5$ each represent an aliphatic or aromatic hydrocarbon residue comprising from 1 to 6 carbon atoms.

5. Process according to claim 1, wherein the azo derivative is selected from among the group comprising derivatives of azobisformamidine, derivatives of azobisformamide, and 1,1'-(azodicarbonyl)-dipiperidine.

6. Process according to claim 1, including the step of applying the azo derivative onto cells at a 10 to 200 micromolar concentration.

7. Process according to claim 6, including the step of applying the azo derivative onto cells at a 10 to 100 micromolar concentration.

8. Process according to claim 1, including the step of applying a composition comprising at least one of the said azo derivatives and an appropriate excipient.

9. Process according to claim 1, including the step of applying said azo derivatives onto cells isolated from macroorganisms or onto cells of microorganisms.

10. Process according to claim 1, including the step of applying said azo derivatives onto cells of an organism or multicellular tissue extracted from a human or animal body.

11. Process according to claim 10, wherein the organism or multicellular tissue is a graft.

12. Process according to claim 1 including the step of applying said at least one azo derivative onto plants.

13. Process according to claim 1, including the step of applying said at least one azo derivative onto animals cells.

14. Process according to claim 1, including the step of applying said at least one azo derivative onto humans cells.

15. Process according to claim 1, including the step of applying said at least one azo derivative onto plant cells.

16. Process according to claim 5, wherein the derivatives of azobisformamidine are selected from the group consisting of 1,1'-azobisformamidine, 1,1'-azobisnitroformamidine, 2,2'-azobismethylformamidine, 1,1'-azobisfluoroformamidine, 1-monochloro-azobisformamidine and azobis.

17. Process according to claim 5, wherein the derivatives of azobisformamide are selected from the group consisting of 1,1'-azobisformamide and dimethylazobisformamide.

18. Method for therapeutic treatment of a human or animal body exhibiting abnormal cellular production of deoxyribonucleic acid, with the exception of those affected by a viral disease, comprising the stage of administration of a therapeutically effective quantity of an active substance to said human or animal body, this active substance being selected from among one or more of the azo derivatives of the formula

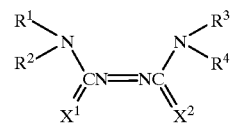

in which $R^1$, $R^2$, $R^3$ and $R^4$ are identical or different and each represents a hydrogen or halogen atom or an optionally substituted aliphatic or aromatic hydrocarbon residue, $R^1$ and $R^2$ possibly being connected together to form a heterocyclic nucleus with the nitrogen atom adjacent thereto, and $R^3$ and $R^4$ possibly being connected together to form a heterocyclic nucleus with the nitrogen atom adjacent thereto, $X^1$ and $X^2$ are identical or different and each represents an oxygen atom or a group $NR^5$, in which $R^5$ is a hydrogen or halogen atom, an optionally substituted aliphatic or aromatic hydrocarbon residue, or a nitro group, and in which, when two groups $NR^5$ are simultaneously present, each $R^5$ may be identical to or different from the other, as well as from among the isomers thereof.

19. Method for therapeutic treatment according to claim 18, wherein said abnormal cellular production is a leukemia or a tumor.

* * * * *